United States Patent

Sato et al.

[11] 4,209,653
[45] Jun. 24, 1980

[54] α-OLEFIN DIMER ISOMERIZATION USING ORGANO-HALOGENS

[75] Inventors: Hiroshi Sato, Toyonaka; Hideto Tojima, Kyoto; Seimei Yasui, Takarazuka, all of Japan

[73] Assignee: Sumitomo Chemical Company, Limited, Osaka, Japan

[21] Appl. No.: 928,978

[22] Filed: Jul. 28, 1978

[30] Foreign Application Priority Data

Aug. 11, 1977 [JP] Japan .................... 52/96679

[51] Int. Cl.² .................... C07C 5/24; C07C 3/21
[52] U.S. Cl. .................................................. 585/313
[58] Field of Search ................. 260/683.2; 585/313

[56]  References Cited
U.S. PATENT DOCUMENTS

| | | | |
|---|---|---|---|
| 3,454,668 | 7/1969 | Down et al. | 260/683.2 |
| 3,542,896 | 11/1970 | Butte | 260/683.2 |
| 3,644,558 | 2/1972 | Wilke et al. | 260/683.2 |
| 3,686,352 | 8/1972 | Neal | 260/683.2 |
| 3,709,953 | 1/1973 | Bergene et al. | 260/683.2 |
| 3,903,188 | 9/1975 | Citron | 260/683.2 |
| 4,155,946 | 5/1979 | Sato et al. | 585/313 |

Primary Examiner—Veronica O'Keefe
Attorney, Agent, or Firm—Birch, Stewart, Kolasch & Birch

[57] ABSTRACT

A process for isomerization of α-olefin dimers which comprises dimerizing a lower α-olefin with a Ziegler type catalyst comprising a nickel compound and an organo-aluminum compound, and then continuing the reaction with addition of at least one compound, prior to deactivation of said catalyst, which is selected from the group consisting of the following organo-halogen compounds of the formulae (I), (II), (III) and (IV),

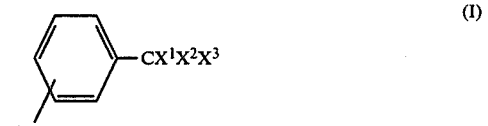

(I)

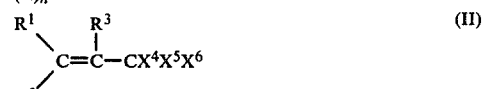

(II)

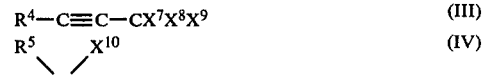

(III)

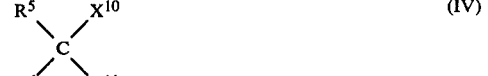

(IV)

wherein $X^1$ to $X^{11}$ are the same or different and are each a halogen or hydrogen atom or an alkyl group having 1 to 20 carbon atoms and at least one of them in each formula is a halogen atom, R is a hydrocarbon group having 1 to 20 carbon atoms, $R^1$, $R^2$ and $R^3$ are the same or different and are each a hydrogen or halogen atom or a hydrocarbon group having 1 to 20 carbon atoms, $R^4$ is a hydrogen atom or a hydrocarbon group having 1 to 20 carbon atoms, $R^5$ and $R^6$ are the same or different and are each an alkyl having 1 to 20 carbon atoms or, taken together, may form a cycloalkyl group, and n is an integer of 0 to 5.

8 Claims, No Drawings

α-OLEFIN DIMER ISOMERIZATION USING ORGANO-HALOGENS

The present invention relates to a process for isomerization of olefins, particularly to isomerization of double bonds. More particularly, it relates to a process for isomerization of olefin dimers comprising dimerizing a lower α-olefin such as ethylene, propylene or butene-1 with a Ziegler type catalyst comprising a nickel compound and an organo-aluminum compound as main components, and then continuing the reaction with addition of an active organo-halogen compound prior to deactivation of said catalyst.

Lower α-olefins such as ethylene, propylene, butene-1 are useful as a starting material for producing high polymers which takes a basic position in the petrochemical industries. Besides, various studies have also been done on dimerization of these α-olefins in order to utilize them in fine chemical industries. For instance, among the isomers of the dimer of propylene, 2-methylpentene can be converted into isoprene by a cracking reaction using a silica-alumina catalyst; 2,3-dimethylbutenes can be dehydrogenated to give 2,3-dimethylbutadiene which is useful as a material for synthetic rubbers and pyromellitic anhydride; and 2-methylpentenes and 2,3-dimethylbutenes can be converted into octane value improving agents by hydrogenation thereof. Moreover it has recently been proposed to use 2,3-dimethylbutene-2 as a material for producing agricultural chemicals. Thus, use of olefin dimers in fine chemical industries is spreading.

In order to use the olefins for such purposes, however, it is not sufficient to merely dimerize the olefins, but it is required to shift the double bonds in the resulting dimers to a desired position. In other words, isomerization of the olefins is essential for utilizing the olefins in fine chemical industries.

The following four processes for dimerizing olefins are known: (1) cationic isomerization using proton acids as a catalyst; (2) cationic isomerization using a combination of Lewis acid and co-catalyst; (3) anionic isomerization using an alkali metal or an alkali metal alcoholate as a catalyst; and (4) isomerization by addition of hydrides and removal thereof using a transition metal as a catalyst.

Among these known processes, the processes (1) and (2) have the following drawbacks: When it is tried to elevate the reactivity of isomerization, it results in occurence of side reactions such as formation of high polymers by an intermolecular reaction, and furthermore, the materials of equipments are undesirably corroded by the acids [cf. C. L. Thomas, Industrial and Engineering Chemistry, Vol. 41, page 2564 (1949)].

The anionic isomerization process (3) is not economical, because it requires a comparatively expensive solvent for the reaction: specific aprotic polar solvents such as dimethylformamide, dimethyl sulfoxide, hexamethyl phosphoric triamide [cf. S. Bank, Journal of the Americal Chemical Society, Vol. 87, page 3245 (1965)].

The process (4) is superior since it proceeds smoothly under mild conditions with little side reaction. However, when the catalyst is a π-allyl type nickel complex as is disclosed in U.S. Pat. No. 3,644,558, it requires troublesome procedures for synthesis of the complex and further the complex is hardly handled since it decomposes in air.

The present inventors have investigated these conventional processes in order to improve them so that after the dimerization of a lower α-olefin is finished, the isomerization can easily be done in the same reaction system. However, it was impossible to proceed smoothly the isomerization while remaining the dimerization catalyst without shortening of the life of isomerization catalysts by poisoning. These conventional processes may be used if the isomerization is carried out after the olefin dimers produced by the dimerization are isolated by rectification, but such a method is not economical since additional procedures are required. The present inventors have further intensively studied in order to find a process for isomerization of the dimers produced by dimerization of lower α-olefins in the same reaction system while remaining the dimerization catalyst, and have surprisinly found that the desired isomerization can very smoothly proceed when a specific active organo-halogen compound is added to the reaction system prior to deactivation of the dimerization catalyst.

An object of the present invention is to provide an improved isomerization process of dimerized olefins.

Another object of the invention is to provide a process for the isomerization of olefins following the dimerization thereof by adding a specific organo-halogen compound to the dimerization system after the dimerization.

These and other objects and advantages of the present invention will be apparent from the following description.

The present invention provides a process for isomerization of α-olefin dimers characterized by dimerizing a lower α-olefin in the presence of a Ziegler type catalyst comprising a nickel compound and an organo-aluminum compund as main components and then continuing the reaction with addition of at least one compound, prior to deactivation of said catalyst, which is selected from the group consisting of the following organo-halogen compounds of the formulae (I), (II), (III) and (IV),

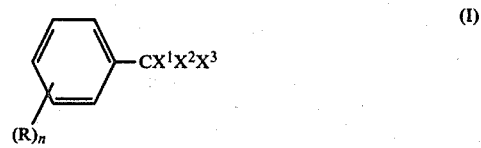

(I)

wherein $X^1$, $X^2$ and $X^3$ are the same or different and are each a halogen or hydrogen atom or an alkyl group having 1 to 20 carbon atoms and at least one of them is a halogen atom, R is a hydrocarbon group having 1 to 20 carbon atoms and n is an integer of 0 to 5,

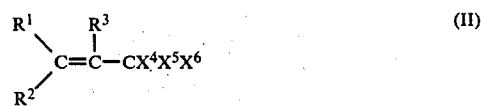

(II)

wherein $R^1$, $R^2$ and $R^3$ are the same or different and are each a hydrogen or halogen atom or a hydrocarbon group having 1 to 20 carbon atoms, $X^4$, $X^5$ and $X^6$ are the same or different and are each a halogen or hydrogen atom or an alkyl group having 1 to 20 carbon atoms and at least one of them is a halogen atom, $$R^4-C\equiv C-CX^7X^8X^9 \quad (III)$$

wherein $R^4$ is hydrogen atom or a hydrocarbon group having 1 to 20 carbon atoms, $X^7$, $X^8$ and $X^9$ are the same or different and are each a halogen or hydrogen atom or an alkyl group having 1 to 20 carbon atoms and at least one of them is a halogen atom, and

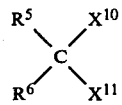
(IV)

wherein $R^5$ and $R^6$ are the same or different and are each an alkyl group having 1 to 20 carbon atoms or, taken together, may form a cycloalkyl group, $X^{10}$ and $X^{11}$ are the same or different and are each a halogen or hydrogen atom or an alkyl group having 1 to 20 carbon atoms and at least one of them is a halogen atom.

In the above formulae, "alkyl group" denotes a straight or branched alkyl having 1 to 20 carbon atoms (e.g. methyl, ethyl, propyl, isopropyl, butyl, tert-butyl, amyl, isoamyl, hexyl, heptyl, octyl, nonyl, decyl, dodecyl, lauryl, stearyl) and a cyclic alkyl having 3 to 7 carbon atoms (e.g. cyclopropyl, cyclobutyl, cyclopentyl, cyclohexyl, cycloheptyl); "hydrocarbon group" denotes a straight or branched alkyl having 1 to 20 carbon atoms as mentioned above, a cyclic alkyl having 3 to 7 carbon atoms as mentioned above, an alkenyl having 2 to 20 carbon atoms (e.g. vinyl, allyl, propenyl, butenyl, pentenyl, hexenyl, heptenyl, octenyl, dodecenyl), an aryl (e.g. phenyl, o-, m- or p-tolyl, xylyl), and an aralkyl (e.g. benzyl, phenethyl); "cycloalkyl" denotes a cyclic alkyl having 3 to 7 carbon atoms as mentioned above; and "halogen" denotes fluorine, chlorine, bromine or iodine.

In the process for dimerization of lower α-olefins such ethylene, propylene and butene with a Ziegler type catalyst comprising a nickel compound and an organo-aluminum compound as main components according to the present invention, the following catalyst systems can be used: the catalyst system comprising nickel acetylacetonate and triethylaluminum as disclosed in U.S. Pat. No. 3,483,268; the catalyst system comprising nickel acetylacetonate, ethylaluminum sesquichloride and trialkyl phosphine as disclosed in U.S. Pat. No. 3,686,352; the catalyst system comprising bis.-trialkyl phosphine.nickel chloride complex and ethylaluminum sesquichloride as disclosed in U.S. Pat. No. 3,467,726; and the catalyst system comprising trihalonickelate complex and ethylaluminum sesquichloride as disclosed in U.S. Pat. No. 3,459,825. More preferably, there is used the catalyst system comprising a nickel compound, triethylaluminum, trialkyl phosphine and halogenated phenol as disclosed in co-pending U.S. Ser. No. 914,291 filed June 9, 1978; now U.S. Pat. No. 4,155,946.

The process of the present invention is characterized in that isomerization is allowed to follow the aforesaid dimerization by adding the organo-halogen compound of the formulae (I) to (IV) to the reaction system after the dimerizaion is finished while the catalyst system for dimerization still keeps its activity. When the foregoing organo-halogen compound is added after the dimerization catalyst is deactivated, for example, by addition of large amounts of alcohol or water, the isomerization does not proceed.

According to the process of the present invention, isomerization of butene-1, which is an ethylene dimer, into butene-2 is of course possible, and also isomerization of 2-methylpentene-1, which is a propylene dimer, into 2-methylpenetene-2, that of 4-methylpentene-1 into 4-methylpentene-2, that of hexene-1 into hexene-2 and hexene-3, and that of 2,3-dimethylbutene-1 into 2,3-dimethylbutene-2 can easily be achieved.

The organo-halogen compounds used for the isomerization of the olefin dimer include various compounds as mentioned below.

The compound of the formula (I) includes benzyl chloride, benzal chloride, benzotrichloride, p-methylbenzyl chloride, o-methylbenzyl chloride, p-nonylbenzyl chloride, o-nonylbenzyl chloride, p-methylbenzal chloride, o-methylbenzal chloride, p-nonylbenzal chloride, o-nonylbenzal chloride, p-methylbenzotrichloride, o-methylbenzotrichloride, p-nonylbenzotrichloride, o-nonylbenzotrichloride, 1-chloromethyl-2,4-dimethylbenzene, 1-chloromethyl-3,4-dimethylbenzene, p-chloromethylstyrene and their fluoro-, bromo- and iodo-homologues. The compound of the formula (II) includes allyl chloride, β-methallyl chloride, crotyl chloride, allyl-α,β-dichloride, 1,2,3-trichloropropene, 1-chloropentene-2, β-chloromethylstyrene and their fluoro-, bromo- and iodo-homologues. The compound of the formula (III) includes propargyl chloride, 1-chlorobutyne-2, 1-chloropentyne-2, 1-chloro-4-methylpentyne-2, β-chloromethylphenylacetylene and their fluoro-, bromo- and iodo-homologues. The compound of the formula (IV) includes tert-butyl chloride, sec-butyl chloride, isopropyl chloride, tert-amyl chloride, tert-heptyl chloride, cyclopropyl chloride, cyclobutyl chloride, cyclopentyl chloride, cyclohexyl chloride and their fluoro-, bromo- and iodo-homologues.

The amount of the aforesaid organo-halogen compounds is not particularly limited, but usually, the organo-halogen compounds are used in an amount of 0.1 to 100 moles, preferably 0.5 to 50 moles, per 1 mole of the organo-aluminum compound in the catalyst system for the dimerization of α-olefins. The molar ratio of the organo-aluminum compound to nickel compound in the catalyst system used in the dimerization of α-olefins is not particularly limited, but is usually within the range of 2 to 500.

The isomerization may be carried out in the presence or absence of a solvent, but usually, the inert solvent used in the foregoing dimerization (e.g. benzene, toluene, n-hexane, n-heptane, chlorobenzene) is used as it is in the isomerization. Since the starting lower α-olefins (e.g. ethylene or propylene) do not give any undesirable effect on the isomerization reaction, there is no problem even if the unreacted starting materials are remained. Accordingly, the isomerization may be carried out without removing the unreacted α-olefins from the dimerization system, or after removing predominantly the unreacted α-olefins from the dimerization system, i.e. after decreasing the inner pressure of reactor by purging the unreacted α-olefins. The isomerization can easily be carried out in either of continuous or batchwise form. The isomerization temperature can be selected within the wide range of about −50° C. to about 200° C., but a temperature between −20° C. and 120° C. is preferred in terms of control of side reactions. A time required for isomerization can optionally be selected depending upon a required isomerization percentage, and it is not particularly limited.

It is necessary that the isomerization is carried out under an atmosphere of inert gas such as nitrogen or argon, and therefore, it should be avoided to proceed the isomerization with mixing a large amount of air or moisture. It is also preferable that the organo-halogen compound added in isomerization is previously deaerated and dehydrated.

The present invention will be illustrated in detail with reference to the following examples, but the present invention is not limited to these examples. In the examples, the composition of α-olefin dimers was analyzed by gas-chromatography (sebaconitrile column: 6 m).

EXAMPLE 1

The atmosphere in a 300 ml stainless steel autoclave equipped with an electromagnetic stirrer was replaced with nitrogen, and 77 ml of dry chlorobenzene, 0.75 ml of toluene solution containing 0.15 mmole of nickel naphthenate and 0.3 ml of toluene solution containing 0.15 mmole of triisopropyl phosphine were added thereto in this order. Some propylene was then dissolved therein at 0° C. by bubbling. Thereafter, 1.44 ml of toluene solution containing 1.5 mmole of ethylaluminum sesquichloride was added thereto, and immediately the autoclave was closed air-tightly. Reaction was carried out at 20° C. for 1.5 hours while maintaining the propylene pressure at 5 kg/cm². After the dimerization was finished, a part of the reaction solution was sampled.

After unreacted propylene was purged, 3 ml of toluene solution containing 1.5 mmole of tert-butyl bromide was added, and the autoclave was closed air-tightly. Isomerization was carried out at 80° C. for 1 hour. During the isomerization, a pressure gauge showed 1.5 kg/cm². After the isomerization was finished, the reaction solution was cooled to room temperature, and isopropanol was added to stop the reaction, followed by washing off the catalyst residue with water. The product was distilled under atmospheric pressure to recover 92 g of propylene dimer. The compositions of the test samples before and after the isomerization were analyzed by gas-chromatography, and the results obtained are shown in Table 1. Isomerization percentage from 2,3-dimethylbutene-1 to 2,3-dimethylbutene-2 was 89.7%.

Table 1

| No. | | 4-Methyl-pentene-2 | 2,3-Dimethyl-butene-1 | 2-Methyl-pentene-1 | Hexene-2 | 2-Methyl-pentene-2 | 2,3-Dimethyl-butene-2 | Based on *2 dimethyl-butenes | Based on *3 2-methyl-penetenes |
|---|---|---|---|---|---|---|---|---|---|
| | | Composition of propylene dimer (%) | | | | | | Isomerization percentage (%) | |
| 1 | Before isomerization | 23.3 | 30.6 | 8.2 | 4.5 | 15.6 | 17.8 | 36.8 | 65.5 |
| 2 | After isomerization | 22.5 | 5.1 | 0.5 | 4.3 | 23.2 | 44.4 | 89.7 | 97.9 |
| 3 | Blank *1 test | 23.0 | 30.5 | 8.0 | 4.2 | 16.3 | 18.0 | 37.1 | 67.1 |

[Remarks]:
*1 After dimerization, reaction was carried out at 80° C. for 1.0 hour with no addition of the organo-halogen compound.

*2 $\frac{2,3\text{-Dimethylbutene-2}}{2,3\text{-Dimethylbutenes}} \times 100$

*3 $\frac{2\text{-Methylpentene-2}}{2\text{-Methylpentenes}} \times 100$

EXAMPLE 2

The atmosphere in a 300 ml autoclave equipped with an electromagnetic stirrer was replaced with nitrogen, and 69 ml of dry chlorobenzene, 0.75 ml of toluene solution containing 0.15 mmole of nickel naphthenate, 0.3 ml of toluene solution containing 0.15 mmole of triisopropyl phosphine, 9 ml of toluene solution containing 2.25 mmole of pentachlorophenol and 0.5 ml of isoprene were added thereto in this order. Thereafter, 1.07 ml of toluene solution containing 1.5 mmole of triethylaluminum was added thereto with stirring, followed by stirring for 5 minutes at room temperature. The autoclave was then closed air-tightly, and dimerization was carried out at 20° C. for 1.5 hours while maintaining the propylene pressure at 5 kg/cm². After the dimerization was finished, a small amount of the reaction solution was sampled for analysis. The unreacted propylene was then purged and 3 ml of toluene solution containing 1.5 mmole of tert-butyl bromide was added thereto. After the autoclave was closed air-tightly, isomerization was carried out for 1 hour at the predetermined temperature shown in Table 2. After the isomerization was finished, the reaction solution was treated in the same manner as in Example 1 to obtain 89 g of propylene dimer. The composition of the isomers was analyzed by gas-chromatography, and the results obtained are shown in Table 2.

Table 2

| No. | | Composition of dimer (%) | | | Composition of 2,3-dimethylbutenes (%) | | |
|---|---|---|---|---|---|---|---|
| | | 2,3-Dimethyl-butenes | 2-Methyl-pentenes | n-Hexenes | 2,3-Dimethyl-butene-1 | 2,3-Dimethyl-butene-2 | Isomerization *2 percentage (%) |
| 1 | Before isomerization | 76.3 | 20.2 | 3.5 | 92.4 | 7.6 | 7.6 |
| 2 | After isomerization at 20° C. | 75.6 | 21.0 | 3.6 | 44.1 | 55.9 | 55.9 |
| 3 | After isomerization at 40° C. | 76.0 | 20.3 | 3.7 | 10.3 | 89.7 | 89.7 |
| 4 | After isomerization at 60° C. | 75.8 | 21.4 | 2.8 | 7.7 | 92.3 | 92.3 |

Table 2-continued

| | | Composition of dimer (%) | | | Composition of 2,3-dimethylbutenes (%) | | |
|---|---|---|---|---|---|---|---|
| No. | | 2,3-Dimethyl-butenes | 2-Methyl-pentenes | n-Hexenes | 2,3-Dimethyl-butene-1 | 2,3-Dimethyl-butene-2 | Isomerization *2 percentage (%) |
| 5 | After isomerization at 80° C. | 76.0 | 20.2 | 3.8 | 7.7 | 92.5 | 92.5 |
| 6 | Blank test at 40° C. *1 | 76.1 | 20.1 | 3.8 | 90.5 | 9.5 | 9.5 |

*1 After dimerization, reaction was carried out at 40° C. for 1.0 hour with no addition of the organo-halogen compound.
*2 Isomerization percentage from 2,3-dimethylbutene-1 to 2,3-dimethylbutene-2

EXAMPLE 3

The atmosphere in a 300 ml autoclave equipped with an electromagnetic stirrer was replaced with nitrogen, and 69 ml of dry chlorobenzene, 0.75 ml of toluene solution containing 0.15 mmole of nickel naphthenate, 0.3 ml of toluene solution containing 0.15 mmole of triisopropyl phosphine and 0.5 ml of isoprene were added thereto in this order. Thereafter, 1.07 ml of toluene solution containing 1.5 mmole of triethylaluminum and 9 ml of toluene solution containing 2.25 mmole of pentachlorophenol were added with stirring in this order. The autoclave was immediately closed airtightly and isomerization was carried out at 20° C. for 1 hour. After the isomerization was finished, the reaction solution was treated in the same manner as in Example 1 to obtain 120 g of propylene dimer. The composition of the isomers was analyzed by gas-chlomatography. The results obtained are shown in Table 3.

Table 3

| | | Composition of dimer (%) | | | Composition of 2,3-dimethylbutenes (%) | | |
|---|---|---|---|---|---|---|---|
| No. | | 2,3-Dimethyl-butenes | Methyl-pentenes | n-Hexenes | 2,3-Dimethyl-butene-1 | 2,3-Dimethyl-butene-2 | Isomerization *2 percentage (%) |
| 1 | Before isomerization | 78.0 | 18.0 | 4.0 | 92.5 | 7.5 | 7.5 |
| 2 | After isomerization | 77.5 | 18.3 | 4.2 | 4.0 | 96.0 | 96.0 |
| 3 | Blank test *1 | 78.0 | 19.0 | 3.0 | 90.0 | 10 | 10 |

*1 After dimerization, reaction was carried out at 20° C. for 1.0 hour with no addition of the organo-halogen compound.
*2 Isomerization percentage from 2,3-dimethylbutene-1 to 2,3-dimethylbutene-2

EXAMPLE 4

Experiment was carried out in the same manner as in Example 3 except that the organo-halogen compounds shown in Table 4 were used in place of benzyl chloride in the isomerization step. The results obtained are shown in Table 4.

Table 4

| | Organo-halogen compound | | | Composition of dimer (%) | | | Composition of 2,3-dimethylbutenes (%) | | |
|---|---|---|---|---|---|---|---|---|---|
| No. | Name | Amount added (mmole) | Isomerization Temperature (°C.) | 2,3-Dimethyl-butenes | Methyl-pentenes | n-Hexenes | 2,3-Dimethyl-butene-1 | 2,3-Dimethyl-butene-2 | Isomerization percentage (%) *2 |
| 1 | Before isomerization | | | 78.0 | 18.0 | 4.0 | 92.5 | 7.5 | 7.5 |
| 2 | Allyl bromide | 2.25 | 80 | 76.5 | 19.0 | 4.5 | 1.5 | 98.5 | 98.5 |
| 3 | Allyl iodide | 2.25 | 80 | 78.0 | 18.5 | 3.5 | 25 | 75.0 | 75.0 |
| 4 | Propargyl bromide | 2.25 | 80 | 77.0 | 18.0 | 5.0 | 9.5 | 90.5 | 90.5 |
| 5 | Propargyl chloride | 2.25 | 40 | 77.0 | 18.0 | 5.0 | 5.0 | 95.0 | 95.0 |
| 6 | Benzyl bromide | 2.25 | 80 | 76.5 | 18.5 | 5.0 | 8.0 | 92.0 | 92.0 |
| 7*1 | Not used | — | 80 | 78.0 | 17.0 | 6.0 | 90.6 | 9.4 | 9.4 |

*1 Blank test (after dimerization of propylene, reaction was carried out at 80° C. for 1 hour with no addition of the organo-halogen compound.
*2 Isomerization percentage from 2,3-dimethylbutene-1 to 2,3-dimethylbutene-2.

tightly. Dimerization was then carried out for 1.5 hours while maintaining the propylene pressure at 5 kg/cm². After the dimerization was finished, a small amount of the reaction solution was sampled for analysis. After unreacted propylene was purged, 1.5 ml of toluene solution containing 1.5 mmole of benzyl chloride was added thereto. The autoclave was then closed air-

EXAMPLE 5

Experiment was carried out in completely the same manner as in Example 3 except that 0.15 mmole of tri-n-butyl phosphine was used in place of triisopropyl phosphine in the dimerization of propylene. The results obtained are shown in Table 5.

Table 5

| | | Composition of dimer (%) | | | Composition of 2,3-dimethylbutenes (%) | | |
|---|---|---|---|---|---|---|---|
| No. | | 2,3-Dimethyl-butenes | Methyl-pentenes | n-Hexenes | 2,3-Dimethyl-butene-1 | 2,3-Dimethyl-butene-2 | Isomerization* percentage (%) |
| 1 | Before isomerization | 39.0 | 57.0 | 4.0 | 93.0 | 7.0 | 7.0 |
| 2 | After | 38.0 | 57.0 | 5.0 | 4.0 | 96.0 | 96.0 |

Table 5-continued

| No. | Composition of dimer (%) | | | Composition of 2,3-dimethylbutenes (%) | | |
|---|---|---|---|---|---|---|
| | 2,3-Dimethyl-butenes | Methyl-pentenes | n-Hexenes | 2,3-Dimethyl-butene-1 | 2,3-Dimethyl-butene-2 | Isomerization* percentage (%) |
| isomerization | | | | | | |

*Content of 2,3-dimethylbutene-2 in 2,3-dimethylbutenes

EXAMPLE 6

Experiment was carried out in the same manner as in Example 3 except that various amounts of tert-butyl chloride shown in Table 6 were used in place of benzyl chloride in the isomerization step. The results obtained are shown in Table 6.

Table 6

| | Organo-halogen compound | | | Composition of dimer (%) | | | Composition of 2,3-dimethylbutenes (%) | | |
|---|---|---|---|---|---|---|---|---|---|
| No. | Name | Amount added (mmole) | Isomerization Temperature (°C.) | 2,3-Dimethyl-butenes | Methyl-pentenes | n-Hexenes | 2,3-Dimethyl-butene-1 | 2,3-Dimethyl-butene-2 | Isomerization percentage (%)* |
| 1 | tert-Butyl chloride | 0.75 | 20 | 74.5 | 21.2 | 4.3 | 5.1 | 84.9 | 84.9 |
| 2 | tert-Butyl chloride | 1.5 | 20 | 76.0 | 20.0 | 4.0 | 4.2 | 95.8 | 95.8 |
| 3 | ter-Butyl chloride | 4.5 | 20 | 75.5 | 19.5 | 5.0 | 4.0 | 96.0 | 96.0 |

*Content of 2,3-dimethylbutene-2 in 2,3-dimethylbutenes

EXAMPLE 7

The atmosphere in a 300 ml autoclave equipped with an electromagnetic stirrer was replaced with nitrogen, and 69 ml of dry chlorobenzene, 0.75 ml of toluene solution containing 0.15 mmole of nickel naphthenate, 5 ml of chlorobenzene solution containing 0.15 mmole of triphenyl phosphine and 0.5 ml of isoprene were added thereto in this order. Thereafter, 1.07 ml of toluene solution containing 1.5 mmole of triethylaluminum was added thereto with stirring, followed by stirring for 5 minutes. Then, 9 ml of chlorobenzene solution containing 2.25 mmole of pentachlorophenol was added, followed by stirring for 5 minutes. The autoclave was closed air-tightly, and dimerization was carried out for 1.5 hours while maintaining the propylene pressure at 5 kg/cm². After the dimerization was finished, a small amount of the reaction solution was sampled for analysis. Thereafter, 1.5 ml of toluene solution containing 1.5 mmole of tert-butyl chloride was added, and the autoclave was closed air-tightly, followed by isomerization at 20° C. for 1 hour. After the reaction was finished, the reaction solution was treated in the same manner as in Example 1 to obtain 85 g of propylene dimer. The compositions of the dimers before and after addition of tert-butyl chloride were as shown in Table 7. Isomerization percentage from 2-methylpentene-1 to 2-methylpentene-2 was 97.6%.

Table 7

| | | Composition of dimer (%) | | | | | |
|---|---|---|---|---|---|---|---|
| No. | | 2,3-Dimethyl-butenes | 4-Methyl-pentene-1 and pentene-2 | n-Hexenes | 2-Methyl-pentene-1 | 2-Methyl-pentene-2 | Isomerization* percentage (%) |
| 1 | Before isomeri-zation | 2.1 | 32.1 | 24.5 | 23.3 | 18.0 | 43.6 |
| 2 | After isomeri-zation | 2.1 | 32.0 | 24.0 | 1.0 | 40.9 | 97.6 |

*Isomerization percentage = $\frac{\text{2-Methylpentene-2}}{\text{2-Methylpentene-1} + \text{2-methylpentene-2}} \times 100$

What is claimed is:

1. In a process for isomerization of a dimer of a lower α-olefin produced by dimerizing the lower α-olefin with a dimerization catalyst comprising a nickel compound and an organo-aluminum compound, the improvement comprising adding at least one compound selected from the group consisting of the following organo-halogen compounds of the formulae (I), (II), (III) and (IV),

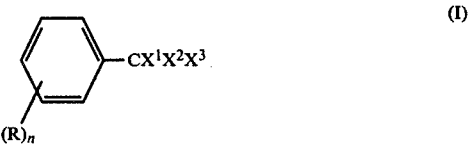

(I)

wherein $X^1$, $X^2$ and $X^3$ are the same or different and are each a halogen or hydrogen atom or an alkyl group having 1 to 20 carbon atoms and at least one of them is a halogen atom, R is a hydrocarbon group having 1 to 20 carbon atoms and n is an integer of 0 to 5,

(II)

wherein $R^1$, $R^2$ and $R^3$ are the same of different and are each a hydrogen or halogen atom or a hydrocarbon group having 1 to 20 carbon atoms, $X^4$, $X^5$ and $X^6$ are the same or different and are each a halogen or hydrogen atom or an alkyl group having 1 to 20 carbon atoms and at least one of them is a halogen atom,

 (III)

wherein $R^4$ is hydrogen atom or a hydrocarbon group having 1 to 20 carbon atoms, $X^7$, $X^8$ and $X^9$ are each a halogen or hydrogen atom or an alkyl group having 1 to 20 carbon atoms and at least one of them is a halogen atom, and

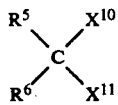 (IV)

wherein $R^5$ and $R^6$ are the same or different and are each alkyl group having 1 to 20 carbon atoms, or taken together, may form a cycloalkyl group having 3 to 7 carbon atoms, $X^{10}$ and $X^{11}$ are the same or different and are each a halogen or hydrogen atom or an alkyl group having 1 to 20 carbon atoms and at least one of them is a halogen atom to the reaction system, prior to deactivation of said dimerization catalyst, in an amount of 0.1 to 100 moles per 1 mole of said organo-aluminum compound in the catalyst, and then continuing the reaction at a temperature of −50° to 200° C. and thereby isomerizing said α-olefin dimer.

2. The process of claim 1 wherein the α-olefin is selected from the group consisting of ethylene, propylene and butene.

3. A process according to claim 1, wherein the amount of the organo-halogen compound is 0.5 to 50 moles per 1 mole of the organo-aluminum compound.

4. A process according to claim 1, wherein the organo-halogen compound of the formula (I) is a member selected from the group consisting of benzyl chloride, benzal chloride, benzotrichloride, p-methylbenzyl chloride, o-methylbenzyl chloride, p-nonylbenzyl chloride, o-nonylbenzyl chloride, p-methylbenzal chloride, o-methylbenzal chloride, p-nonylbenzal chloride, o-nonylbenzal chloride, p-methylbenzotrichloride, o-methylbenzotrichloride, p-nonylbenzotrichloride, o-nonylbenzotrichloride, 1-chloromethyl-2,4-dimethylbenzene, 1-chloromethyl-3,4-dimethylbenzene, p-chloromethylstyrene and their fluoro- bromo- and iodo-homologues.

5. A process according to claim 1, wherein the organo-halogen compound of the formula (II) is a member selected from the group consisting of allyl chloride, β-methallyl chloride, crotyl chloride, allyl-α,β-dichloride, 1,2,3-trichloropropene, 1-chloropentene-2, β-chloromethylstyrene and their fluoro-, bromo- and iodo-homologues.

6. A process according to claim 1, wherein the organo-halogen compound of the formula (III) is a member selected from the group consisting of propargyl chloride, 1-chlorobutyne-2, 1-chloropentyne-2, 1-chloro-4-methylpentyne-2, β-chloromethylphenylacetylene and their fluoro-, bromo and iodo-homologues.

7. A process according to claim 1, wherein the organo-halogen compound of the formula (IV) is a member selected from the group consisting of tert-butyl chloride, sec-butyl chloride, iso-propyl chloride, tert-amyl chloride, tert-heptyl chloride, cyclopropyl chloride, cyclobutyl chloride, cyclopentyl chloride, cyclohexyl chloride and their fluoro-, bromo- and iodo-homologues.

8. A process according to claim 1, wherein the isomerization temperature is in the range of from −20° to 120° C.

* * * * *